United States Patent
Zheng et al.

(10) Patent No.: US 10,912,846 B2
(45) Date of Patent: Feb. 9, 2021

(54) MOLECULAR PROBES FOR CHEMILUMINESCENCE IMAGING AND IN VIVO DETECTION OF TARGET MOLECULES

(71) Applicant: ARIZONA BOARD OF REGENTS ON BEHALF OF THE UNIVERSITY OF ARIZONA, Tucson, AZ (US)

(72) Inventors: Zhiping Zheng, Tucson, AZ (US); Jiagen Lv, Xi'an (CN); Yingchun Nie, Xi'an (CN); Wansheng Liang, Lanzhou (CN)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 559 days.

(21) Appl. No.: 15/578,042

(22) PCT Filed: May 27, 2016

(86) PCT No.: PCT/US2016/034810
§ 371 (c)(1),
(2) Date: Nov. 29, 2017

(87) PCT Pub. No.: WO2016/196359
PCT Pub. Date: Dec. 8, 2016

(65) Prior Publication Data
US 2018/0161460 A1    Jun. 14, 2018

Related U.S. Application Data (60) Provisional application No. 62/168,137, filed on May 29, 2015.

(51) Int. Cl.
| | | |
|---|---|---|
| *A61B 5/00* | (2006.01) | |
| *A61B 8/00* | (2006.01) | |
| *A61B 10/00* | (2006.01) | |
| *A61K 49/00* | (2006.01) | |
| *C07D 405/04* | (2006.01) | |

(52) U.S. Cl.
CPC ........ *A61K 49/0043* (2013.01); *C07D 405/04* (2013.01)

(58) Field of Classification Search
CPC ................................................. A61K 49/0043
See application file for complete search history.

(56) References Cited

U.S. PATENT DOCUMENTS

| 5,019,496 A | 5/1991 | Oster et al. |
| 2006/0030054 A1 | 2/2006 | Nagano et al. |
| 2012/0207684 A1 | 8/2012 | Basilion et al. |

FOREIGN PATENT DOCUMENTS

| WO | WO2006094187 A2 | 9/2006 |
| WO | WO2009124024 A1 | 10/2009 |
| WO | WO2012127441 A1 | 9/2012 |

OTHER PUBLICATIONS

Agarwal, A., Shyam, S. R. & Allamaneni, T. M. S. Chemiluminescence technique for measuring reactive oxygen species. Reprod. Biomed. Online 9, 466-468 (2004).
Blow, N. In vivo molecular imaging: the inside job. Nat. Methods 6, 465-469 (2009).
Bonekamp, D., Hammoud, D. A. & Pomper, M. G. Molecular imaging, techniques and current clinical applications. Appl. Radiol. 39, 10-21 (2010).
Bourzac, K. Medical imaging: Removing the blindfold. Nature 504, S10-S12 (2013).
Campbell, A. K. in Chemiluminescence: principles and applications in biology and medicine. Ellis Horwood: Chichester, 68-126 (1988).
Chapman, S. et al. Nanoparticles for cancer imaging: the good, the bad, and the promise. Nano Today 8, 454-460 (2013).
Chatterjee, S. & Fisher, A. B. ROS to the rescue. Am. J. Physiol. 287, L704-L705 (2004).
Chen, W., Tung, C. & Weissleder, R. Imaging reactive oxygen species in arthritis. Mol. Imaging. 3, 159-162 (2004).
Cheng, Z., Zaki, A. A., Hui, J. Z., Muzykantov, V. R. & Tsourkas, A. Multifunctional nanoparticles: cost versus benefit of adding targeting and imaging capabilities. Science 338, 903-910 (2012).
Dothager, R. S. & Piwnica-Worms, D. Nano in cancer: linking chemistry, biology, and clinical applications in vivo. Cancer Res. 71, 5611-5615 (2011).
Dothager, R. S. et al. Advances in bioluminescence imaging of live animal models. Curr. Opin. Biotechnol. 20, 45-53 (2009).
Eutick, M. Sodium fluorescein—colorful past, bright future. J. Ophthalmic. Photogr. 28, 66-70 (2006).
Ganguly, D., Chacraborty, S., Balitanas, M. & Kim, T.-h. Medical imaging: a review. In Kim, T.-H., Stoica, A. & Chang, R.-S. (eds.): Security-enriched urban computing and smart grid communications, computer and information science. 78, 504-516 (2010); Springer-Verlag Berlin Heidelberg.
Gross, S. et al. Bioluminescence imaging of myeloperoxidase activity in vivo. Nat. Med. 4, 455-461 (2009).
Hargreaves, R. J. The role of molecular imaging in drug discovery and development. Clin. Pharmacol. Ther. 83, 349-353 (2008).

(Continued)

*Primary Examiner* — Michael G. Hartley
*Assistant Examiner* — Melissa J Perreira
(74) *Attorney, Agent, or Firm* — Nguyen Tarbet LLC (57) ABSTRACT

Chemiluminescence imaging probes for in vivo detection of biological molecules, events, or processes. The CLI probes may feature a portion of a fluorescein molecule and a portion of a luminol molecule. The fluorescein molecule and luminol molecule may be linked by a non-xanthenic aromatic ring. The CLI probes are generally non-toxic and soluble in aqueous solutions such as PBS. The CLI probes may be used to detect specific molecules in vivo.

10 Claims, 9 Drawing Sheets
(7 of 9 Drawing Sheet(s) Filed in Color)

(56) References Cited

OTHER PUBLICATIONS

Hastings, J. W. & Johnson, C. H. Bioluminescence and chemiluminescence. Meth. Enzymol. 360, 75-104 (2003).

Heffern, M. C., Matosziuk, L. M. & Meade, T. J. Lanthanide probes for bioresponsive imaging. Chem. Rev. 114, Article ASAP (2014); DOI: 10.1021/cr400477t.

Heindl, D. & Josel, H.-P. in Nonradioactive analysis of biomolecules. Springer lab manuals, 258-261; Springer-Verlag Berlin Heidelberg (2000).

Jiao, G., Castro, J. C., Thoresen, L H. & Burgess, K. Microwave-assisted syntheses of regioisomerically pure bromorhodamine derivatives. Org. Lett. 5, 3675-3677 (2003).

Kielland, A. et al. In vivo imaging of reactive oxygen and nitrogen species in inflammation using the luminescent probe L-012. Free Radical Biol. Med. 47, 760-766 (2009).

Lee, D. et al. In vivo imaging of hydrogen peroxide with chemiluminescent nanoparticles. Nat. Mater. 6, 765-769 (2007).

Lee, Y. et al. Dye/peroxalate aggregated nanoparticles with enhanced and tunable chemiluminescence for biomedical imaging of hydrogen peroxide. ACS Nano 8, 6759-6766 (2012).

Lequin, R. Enzyme immunoassay (EIA)/enzyme-linked immunosorbent assay (ELISA). Clin. Chem. 51, 2415-2418 (2005).

Li, C. A targeted approach to cancer imaging and therapy. Nat. Mater. 13, 110-115 (2014).

Lim, C. et al. Chemiluminescence-generating nanoreactor formulation for near-infrared imaging of hydrogen peroxide and glucose level in vivo. Adv. Funct. Mater. 20, 2644-2648 (2010).

Louie, A. Multimodality imaging probes: design and challenges. Chem. Rev. 110, 3146-3195 (2010).

Luker, G. D. & Luker, K. E. Optical imaging: current applications and future directions. J. Nucl. Med. 49, 1-4 (2008).

Luker, K. E. & Luker, G. D. Applications of bioluminescence imaging to antiviral research and therapy: multiple luciferase enzymes and quantitation. Antiviral Res. 78, 179-187 (2008).

Massoud, T. F. & Gambhir, S. S. Molecular imaging in living subjects: seeing fundamental biological processes in a new light. Genes & Dev. 17, 545-580 (2003).

Merényi, G., Lind, J. & Eriksen, T. E. Luminol chemiluminescence: chemistry, excitation, emitter. J. Biolumin. Chemilumin. 5, 53-56 (1990).

Mueller, K. Inflammation's yin-yang. Science 339, 155-155 (2013).

Prescher, J. A. & Contag, C. H. Guided by the light: visualizing biomolecular processes in living animals with bioluminescence. Curr. Opin. Chem. Biol. 14, 80-89 (2010).

Pysz, M. A., Gambhir, S. S. & Willmann, J. K. Molecular imaging: current status and emerging strategies. Clin Radiol. 65, 500-516 (2010).

Ricchiuti, V. Immunoassay-based technologies for the measurement of biological materials used for biomarkers discovery and translational research in Vaidya, V. S. & Bonventre, J. V. (eds): Biomarkers: in medicine, drug discovery and environmental health. 425-455 (2010).

Roda, A., Guardigli, M., Michelini, E. & Mirasoli, M. Bioluminescence in analytical chemistry and in vivo imaging. Trends Anal. Chem. 28, 307-322 (2009).

Rudin, M. & Weissleder, R. Molecular imaging in drug discovery and development. Nat. Rev. 2, 123-131 (2003).

Thorpe, G. H. G. & Kncka, L. J. Enhanced chemiluminescent reactions catalyzed by horseradish peroxidase. Meth. Enzymol. 133, 331-353 (1986).

Tseng, J. & Kung, A. L. In vivo imaging of inflammatory phagocytes. Chem. Biol. 19, 1199-1209 (2012).

Zhou, J., Tsai, Y.-T., Weng, H. & Tang, L. Noninvasive assessment of localized inflammatory responses. Free Radic. Biol. Med. 52, 218-226 (2012).

FIG. 1A

Formula 1

| ROS | $^1O_2$ | $O_2^-$ | HO· | ClO⁻ | $H_2O_2$-HRP | $H_2O_2$ |
|---|---|---|---|---|---|---|
| $S_{Probe3}{}^a$ | 226785 | 107220 | 44868 | 264384 | 11427432 | 3701160204 |
| $S_{Luminol}{}^a$ | 8806 | 2050 | 427 | 1652 | 551976 | 484715 |
| $S_{Probe3}/S_{Luminol}{}^b$ | 25.75 | 52.30 | 105.08 | 160.04 | 20.8 | 7636 | a. Integration area under the CL dynamic curve represents the total CL emission.

b. As the relative CL capability of probe 3 in comparison with luminol to each ROS.

FIG. 7

(a) Urine discharge of probe 3 (%) of dose over time

| In hour | 1st | 2nd-3rd | 4th-5th | 6th-7th | Total | After 7th |
|---|---|---|---|---|---|---|
| Excretion (%) of dose | 59.0 | 32.3 | 5.4 | 1.0 | 97.7 | undetectable |

(b) Urine discharge of molecular 2 (%) of dose over time

| In hour | 1st | 2nd | 3rd | 4th | Total | After 4th |
|---|---|---|---|---|---|---|
| Excretion (%) of dose | 65.5 | 13.0 | 10.1 | 1.0 | 90.4 | undetectable |

MOLECULAR PROBES FOR CHEMILUMINESCENCE IMAGING AND IN VIVO DETECTION OF TARGET MOLECULES

CROSS REFERENCE

This application is a 371 application and claims benefit of International Patent Application No. PCT/US16/34810 filed May 27, 2016, which claims benefit of U.S. Provisional Patent Application No. 62/168,137 filed May 29, 2015, the specification(s) of which is/are incorporated herein in their entirety by reference.

FIELD OF THE INVENTION

The present invention relates to chemiluminescence imaging (CLI) and CLI probes, more particularly to probes for CLI and CLI probes for the in vivo detection and/or monitoring of biological processes.

BACKGROUND OF THE INVENTION

In biological applications, chemiluminescence imaging (CLI) is commonly used for in vitro detection of target molecules, e.g., using techniques such immunoassays, protein blotting, pharmacological tests, and the like. In many cases, CLI involves the reaction of luminol and hydrogen peroxide ($H_2O_2$), which emits light. Or, CLI may utilize other compounds such as luciferin, aequorin, or others. CLI probes are presently used for the detection of reactive oxygen species (ROS), such as hydrogen peroxide, however clinical applications, e.g., in vivo applications, of CLI beyond ROS detection have been limited.

Inventors have surprisingly discovered a molecular chemiluminescence imaging (CLI) probe for use in CLI applications, including in vivo applications. Such in vivo applications may include but are not limited to the detection of, the localization of, and/or the quantification of various target molecules of interest, e.g., inflammatory molecules or any other appropriate molecule of interest.

SUMMARY OF THE INVENTION

The present invention features chemiluminescence imaging (CLI) probes. In some embodiments, the CLI probe comprises a fluorescein molecule linked to a luminol molecule (e.g., an amine-less luminol molecule). In some embodiments, the fluorescein molecule is linked to a luminol molecule via a non-xanthenic aromatic ring. In some embodiments, the CLI probe is according to Formula 1 (e.g., Compound 3/Probe 3) or a derivative thereof.

For example, in some embodiments, the chemiluminescence imaging (CLI) probe is according to Formula 1 (see FIG. 1A and see below). In some embodiments, any of R1-R8 are —H, —OH, —COH, —COOH, or a halide. In some embodiments, the CLI probe comprises Compound 3 (see FIG. 1B and see below).

Formula 1

Compound 3

In some embodiments, R1 is —H, —OH, —COH, —COOH, or a halide. In some embodiments, R2 is —H, —OH, —COH, —COOH, or a halide. In some embodiments, R3 is —H, —OH, —COH, —COOH, or a halide. In some embodiments, R4 is —H, —OH, —COH, —COOH, or a halide. In some embodiments, R5 is —H, —OH, —COH, —COOH, or a halide. In some embodiments, R6 is —H, —OH, —COH, —COOH, or a halide. In some embodiments, R7 is —H, —OH, —COH, —COOH, or a halide. In some embodiments, R8 is —H, —OH, —COH, —COOH, or a halide.

The CLI probes may be generally soluble, e.g., in PBS or other aqueous solutions. The CLI probes may be generally non-toxic.

The present invention also features kits comprising a CLI probe of the present invention. In some embodiments, the kit further comprises a reactive oxygen species (ROS), e.g., hydrogen peroxide ($H_2O_2$) or any other appropriate ROS. In some embodiments, the kit further comprises a first binding molecule labeled (e.g., an antibody, an antibody fragment, ligand, any other appropriate detection/binding molecule, etc.). In some embodiments, the first binding molecule is labeled with a ROS, e.g., $H_2O_2$ or any other appropriate ROS). In some embodiments, the kit comprises a CLI probe according to Formula 1 and a first binding molecule labeled with horseradish peroxidase (HRP) or other appropriate label, e.g., myeloperoxidase (MPO).

The present invention also features a method of producing chemiluminescence. In some embodiments, the method comprises reacting a CLI probe of the present invention with an ROS (e.g., $H_2O_2$ or any other appropriate ROS).

The present invention also features a method of detecting inflammation in a subject. In some embodiments, the method comprises introducing to the subject a CLI probe of the present invention. The method may further comprise introducing to the subject a first binding molecule labeled with an ROS (e.g., $H_2O_2$ or any other appropriate ROS). In some embodiments, the first binding molecule is specific for an inflammatory molecule. As the CLI probe is adapted to be oxidized by the ROS thereby emitting chemiluminescence, chemiluminescence may be indicative of the presence of the inflammatory molecule. In some embodiments, the CLI probe is administered before the first binding molecule is administered. In some embodiments, the first binding molecule is administered before the CLI probe is administered.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE DRAWINGS

This patent application contains at least one drawing executed in color. Copies of this patent or patent application publication with color drawing(s) will be provided by the Office upon request and payment of the necessary fee.

FIG. 5 shows kinetics of the luminescence resulting from the oxidation of probe 3 by various ROS. Solutions of 3 and luminol were prepared in 0.01 M PBS (pH of 7.4). For all ROS other than $H_2O_2$, the reaction was carried out by mixing 200 µL of the ROS solution (1.0×10$^{-3}$ M) with 800 µL of the solution of probe 3 or luminol (1.0×10$^{-6}$ M). The voltage of the photomultiplier tube (PMT) was set at −400 V. In the case of $H_2O_2$, 200 µL of its solution (1.0×10$^{-2}$ M) was used, and the voltage of PMT was set at −800 V; all other conditions were identical to those used for the other ROS. Non-$H_2O_2$ ROS, including ClO$^-$, HO., $O_2.^-$ and $^1O_2$, all showed much stronger responses to probe 3 than to luminol with similar kinetics; all reactions completed within about 20 seconds. The reaction with $H_2O_2$ displayed a much sluggish kinetics despite the fact that the concentration of $H_2O_2$ was 10 times as much as the other ROS. In fact, only when the voltage of the PMT was set at −800 V could the chemiluminescence be detected. For the PMT used in this work, this difference in voltage, −400 V versus −800 V, is equivalent to 2000-5000 fold of difference in luminescence intensity. The need to increase the detection voltage of the PMT thus indicates the insensitivity of probe 3 toward $H_2O_2$ when compared with the other ROS. It is noted that for $H_2O_2$, the luminescence resulting from the reaction with luminol decayed to the baseline in about 600 s, whereas that with probe 3 lasted for more than 18 days. Integrating the areas under the CL decay curves results in the quantum yield ratios between probe 3 and luminol with various ROS, collected in FIG. 6.

FIG. 6 shows in vitro CL response of probe 3 when oxidized by various ROS (as PBS solution at pH 7.4). The ROS were generated according to literature procedures. Chemiluminescence decay curves were recorded using a MPI-A chemiluminescence spectrometer, and the data were integrated by using the software accompanying the spectrometer. Results shown are the average of three independent measurements.

FIG. 7 shows quantification of probe 3 and the oxidation product 2 (ground-state luminophore) in the urine discharge of test mice. Nude mice (24-26 g) were anesthetized followed by intraperitoneal injection of 3 or 2 (in 0.01 M PBS pH 7.4) using a dose of 660 µg of 3 or 2 per kilogram of the mouse body weight. The mice were housed individually and received food ad libitum. Urine was collected every 1 to 2 hours, and the collected samples were diluted to appropriate concentration with PBS. Probe 3 in each urine sample was quantified by comparing the intensity of its chemiluminescence resulting from its oxidation by NaClO with those of standard solutions. The results are summarized in (a). Compound 2 was quantified by fluorescence method, and the results were collected in (b). The potential toxicity of the probe was further evaluated with a sample of 50 mice using a dose of probe 3 at 72 mg/kg body weight of mouse. This amount is 100 fold of the dose used in typical CLI experiments. No death or abnormal behavior of any of the test mice was observed after six months of the probe administration, indicating that the acute toxicity of the probe, if any, is insignificant, and may be attributed to the facile discharge through urination.

FIG. 8 shows the oxidation of probe 3 by $H_2O_2$ was significantly catalyzed by a trace amount of HRP. The control reaction with no HRP (blue baseline) is sluggish with no detectable luminescence (probe 3: 5.0×10$^{-3}$ M; $H_2O_2$ 1.0×10$^{-4}$ M). When a trace amount of HRP (5.0×10−5 mg/mL) was added (as indicated by the arrow pointing at the purple curve), the oxidation reaction was promoted, and within seconds, progressed rapidly with the intense emission of a green light.

FIG. 9A shows imaging of HRP with a lower concentration of probe compound 3. CLI of HRP in the same nude mouse with the use of compound 3 as probe (7.2 mg per kg body weight, intraperitoneally injected). Against PBS-only control in the left foreleg, the total activity of HRP introduced into the right foreleg, the left hind leg, and the right hind leg were 0.0250, 0.125, and 0.250 U, respectively. The moment when the administration of 3 was completed was set as −20 min (panel (i)) with 0 min (panel (ii)) being the moment when the subcutaneous injection of HRP was finished. The circles in panel (ii) indicate both the sites of HRP introduction and the ROI for which photon-counting integration was performed.

FIG. 9B shows the brightness of CL produced. The brightness of CL produced was measured 60 minutes after the administration of HRP. Data presented as mean±s.e.m. (n=3 mice per group). $I_{total\ flux}=2.34\times10^5\ U_{HRP}+4.9\times10^3$.

FIG. 11 shows in vitro sensitive response of probe 3 to phagocyte respiratory burst. No chemiluminescence was detected in the absence of phorbol 12-myristate 13-acetate for (PMA) or N-formylmethionyl-leucyl-phenyl-alanine (FMLP). (a) CL kinetics resulting from the response of probe 3 to respiratory burst of raw 264.7 cells when stimulated with PMA (100 μg/ml). (b) CL kinetics resulting from the response of probe 3 to respiratory burst of human monocyte (106 cells/ml) in hank's when stimulated by FMLP (100 μg/ml). The kinetics curves were recorded with an MPI-A Chemiluminescence Analyzer with the use of probe 3 or luminol ($5.0\times10^{-5}$ M). These results suggest that probe 3 is a much more sensitive probe for the detection of ROS than luminol.

DESCRIPTION OF PREFERRED EMBODIMENTS

Referring now to FIG. 1-12, the present invention features novel chemiluminescence imaging (CLI) probes for CLI applications including but not limited to clinical applications and the in vivo detection of biological processes.

Figure 1A:
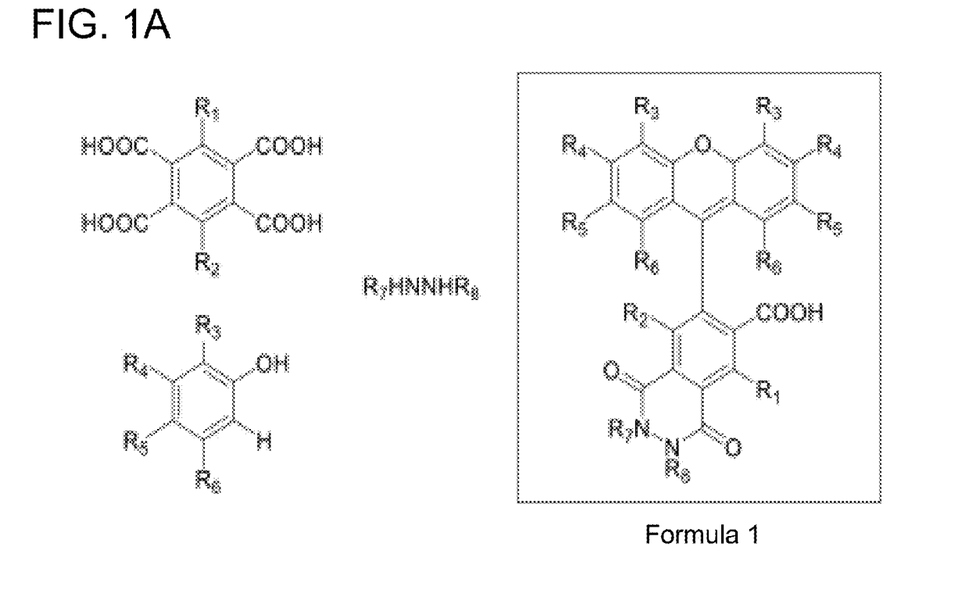
FIG. 1A shows examples of structures of the CLI probe (Formula 1, shown on right) of the present invention (note that Compound 3 is an example of Formula 1). The probe is synthesized from starting materials shown on the left.
Figure 1B:
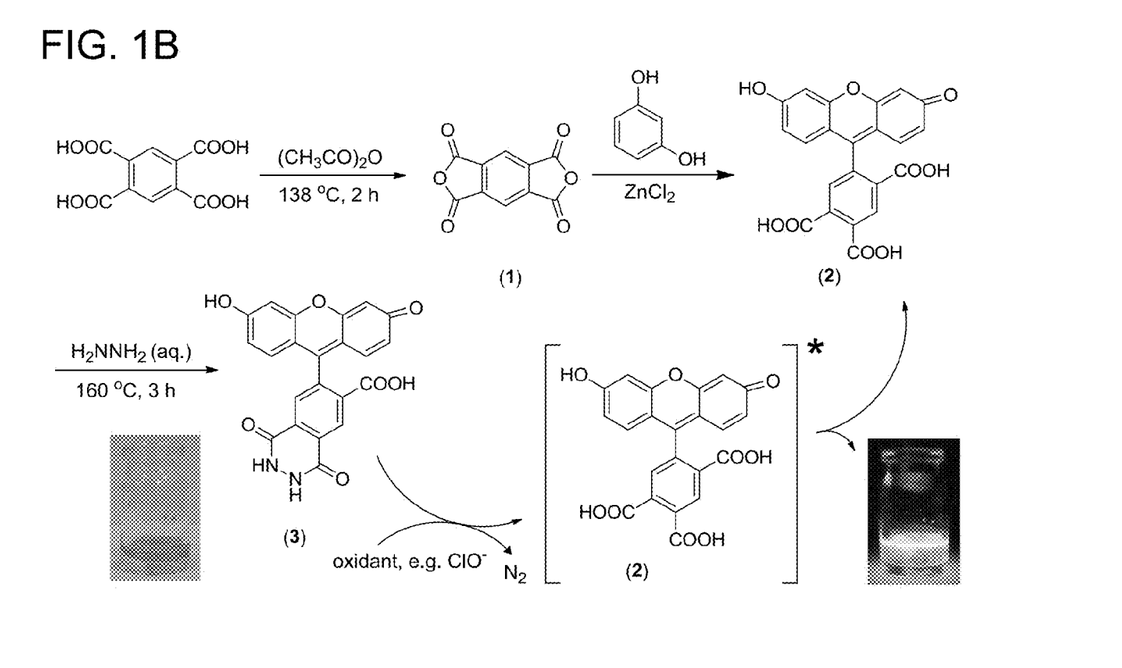
FIG. 1B shows synthesis of a CLI probe (compound 3). Its oxidation (1.0 mM in 0.1 M NaOH) by NaClO produced the excited-state luminophore (compound 2) that decayed to luminesce vividly in green at $\lambda_{max}$=530 nm.

FIG. 1A shows a CLI probe according to Formula 1. The probe can be synthesized using starting materials shown on the left of FIG. 1A. Non-limiting examples of synthesis can be found in FIG. 1B and Example 1 below. FIG. 1B shows synthesis of a CLI probe of the present invention (compound 3). In some embodiments, Formula 1 (e.g., Compound 3) comprises a fluorescein molecule and a luminol analog (e.g., an amine-less luminol molecule) connected via a non-xanthenic aromatic ring. The probe can be activated by reaction with an oxidant such as but not limited to ROS to generate a product at its excited state. Light is emitted when the product relaxes to its ground state. Without wishing to limit the present invention to any theory or mechanism, it is believed that modification of the xanthenic moiety of fluorescein with the luminol-like functional group helps the CLI probe to respond to reactive oxygen species (ROS).

In Formula 1, substituents $R_1$-$R_8$ may be any common organic group (e.g. alkyl group, —OH, —COH/R, or —COOH/R, etc.) or inorganic functional group (e.g., halides) that are compatible with the synthesis including steric requirement. In some embodiments, the functional groups may be selected for particular properties, e.g., reaction kinetics (e.g., the excitation or oxidation of the probe to the product at its excited and emissive state, the relaxation from the product at the excited state to the relaxed state with the accompanying emission of light, etc.), the color of emitted light, the ability to tune the color of emission, etc.

The CLI probe (e.g., Formula 1, e.g., compound 3) is readily soluble in both alkaline and phosphate-buffered saline solutions (PBS, e.g., pH=7.4). Oxidation of compound 3 was accompanied by vivid green luminescence when the excited oxidation product (compound 2) underwent deactivation (see FIG. 1). FIG. 1B (bottom right corner) shows a bright CL emission resulting from the oxidation of compound 3 by NaClO, a representative ROS, in aqueous NaOH.

Figure 2:
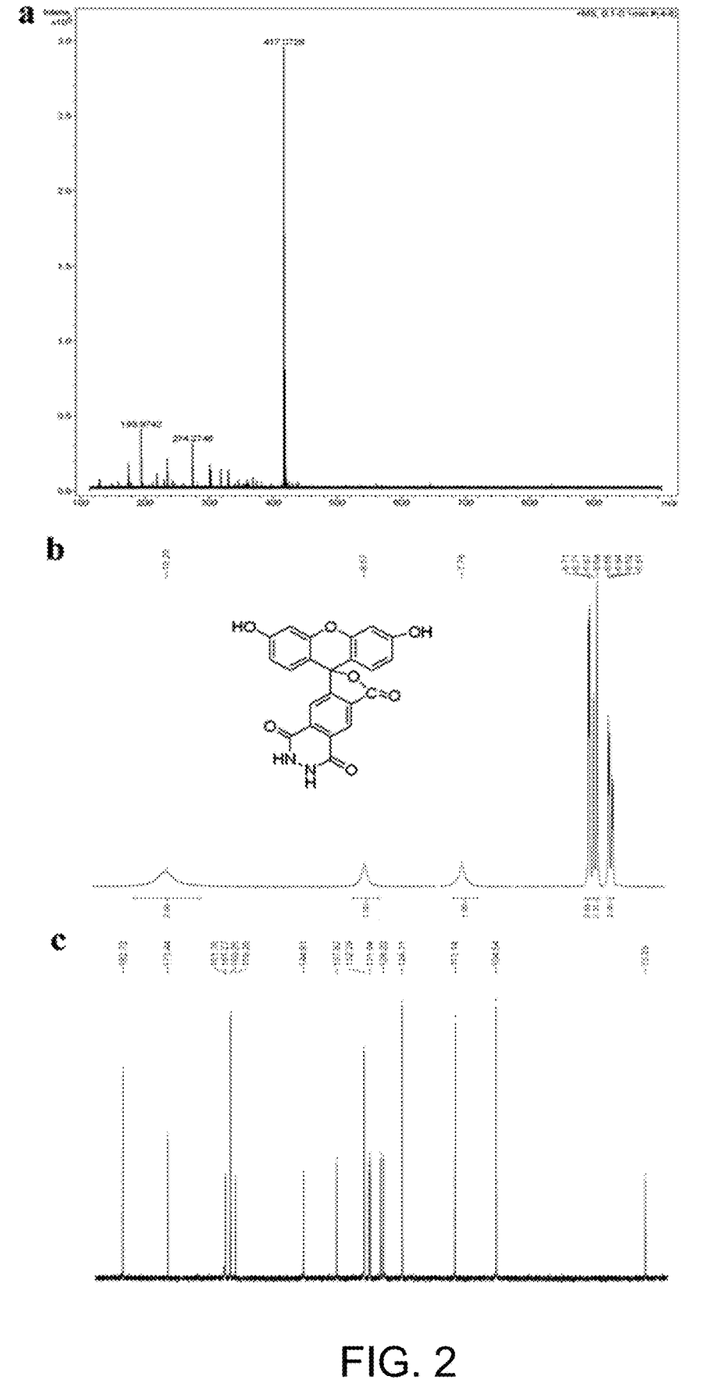
FIG. 2 shows the characterization of compound 3: (a) high-resolution mass spectrometry data; (b) $^1$H NMR spectrum; and (c) $^{13}$C NMR spectrum.
Figure 3:
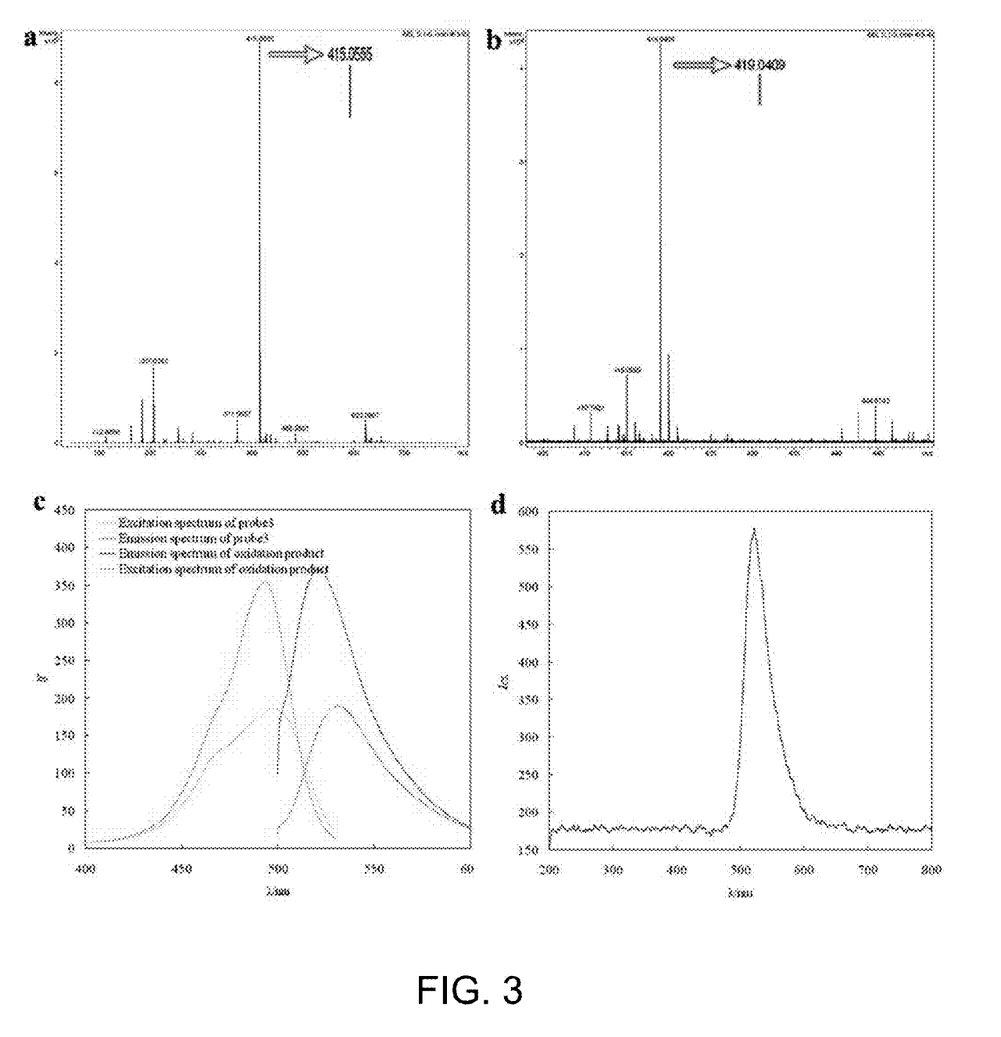
FIG. 3 shows the oxidation of probe 3 leading to the production of luminophore 2. (a) HRMS of probe 3: [M−H]$^-$ 415.0555. (b) HRMS of the product from the oxidation of probe 3 (probe 3+$H_2O_2$+HRP, reacted for 30 min): The peak of [M−H]$^-$ at 419.0409 corresponds to compound 2. (c) Fluorescence spectra of probe 3 (1.0×10-5 M) and compound 2 (1.0×10$^{-6}$ M) in aqueous NaOH (0.01 M). (d) Chemiluminescence spectrum of probe 3 (1.0×10$^{-5}$ M probe 3+1.0×10$^{-3}$ M NaClO). Disappearance of the m/z peak at 415.0555 and the newly appeared peak at 419.0409 suggested the complete oxidation of probe 3 with compound 2 being the product. This analysis is consistent with the luminescence studies shown in (c) and (d) (above): The chemiluminescence peak in (d) matches that of compound 2. It could be concluded that the oxidation probe 3 lead to the production of the luminophore, that is, compound 2 at its excited state.

FIG. 2 shows the characterization of compound 3: (a) high-resolution mass spectrometry data; (b)$^1$H NMR spectrum; and (c)$^{13}$C NMR spectrum. FIG. 3 shows the oxidation of probe 3 leading to the production of luminophore 2.

The CLI probes of the present invention may be used in combination with complexes such as but not limited to ligands (specific for a target of interest) labeled with HRP or other appropriate molecule. For example, the HRP linked to a ligand (which may be bound to its target) can catalyze the oxidation of the CLI probe (e.g., compound 3). Thus, in some embodiments, the CLI probes of the present invention may be used for detecting (e.g., amount of or presence of or location of) a biological event, e.g., the amount and/or location of the chemically generated light can be used to detect or analyze specific biological events.

Figure 4:
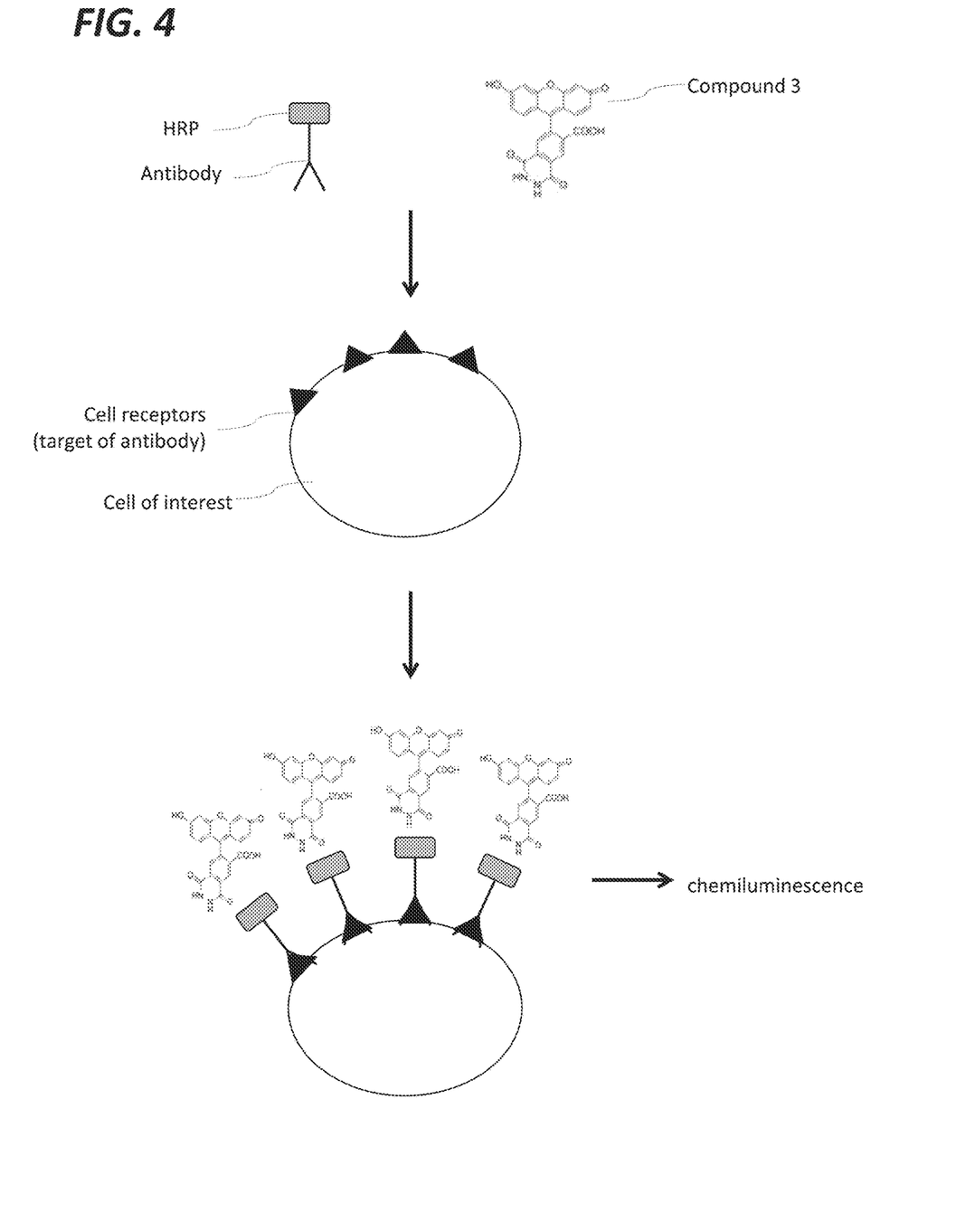
FIG. 4 shows a schematic representation of in vivo detection of receptor molecules on a target cell of interest. The present invention is not limited to the components or methods shown in FIG. 4.
Figure 5:
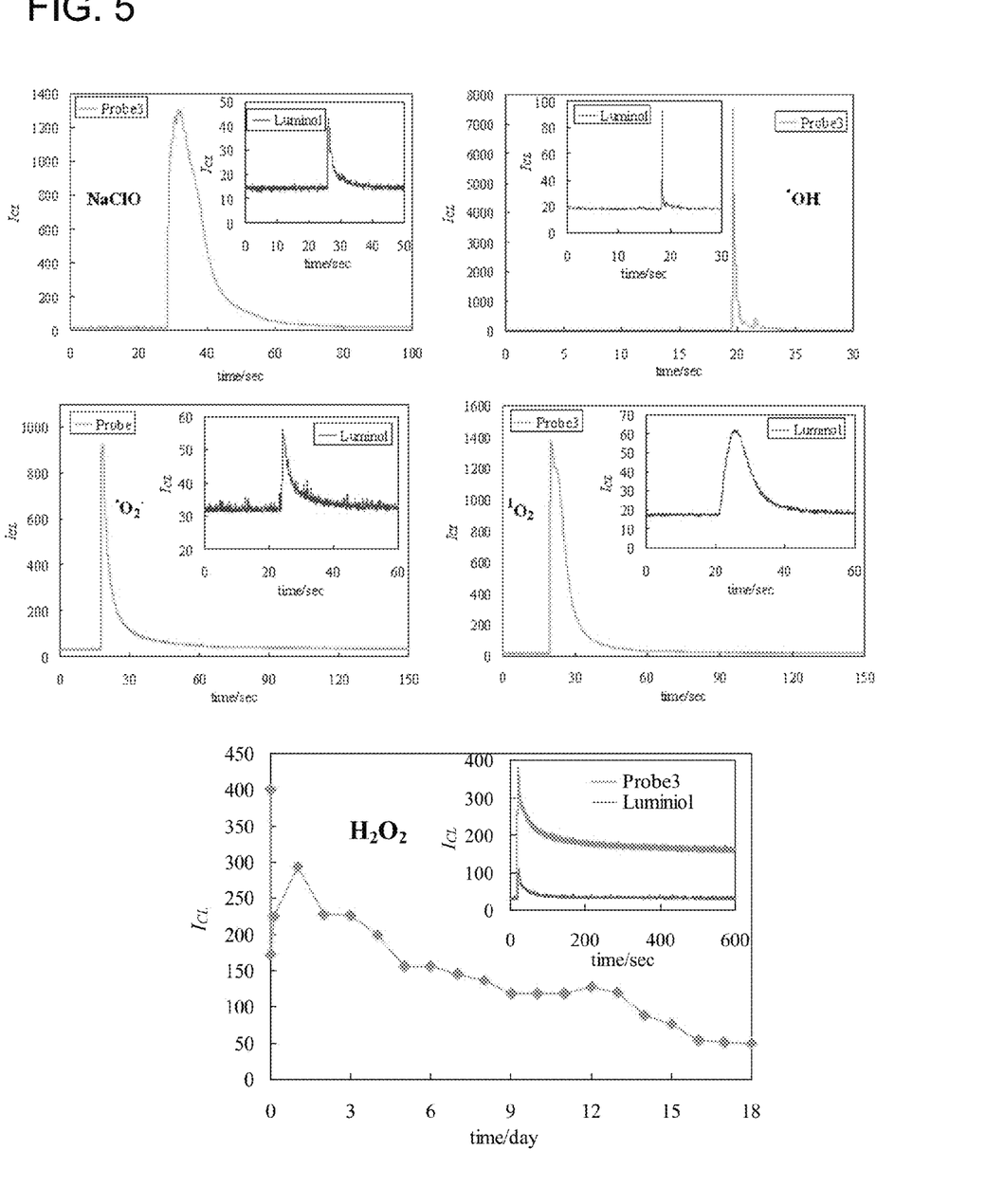
Figure 6:
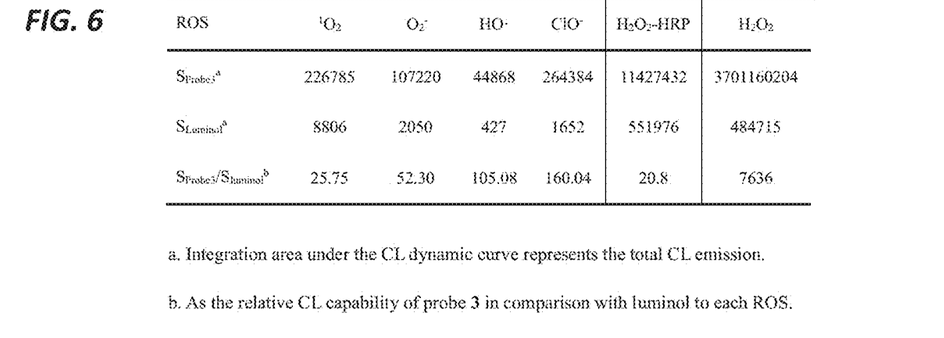
Figure 7:
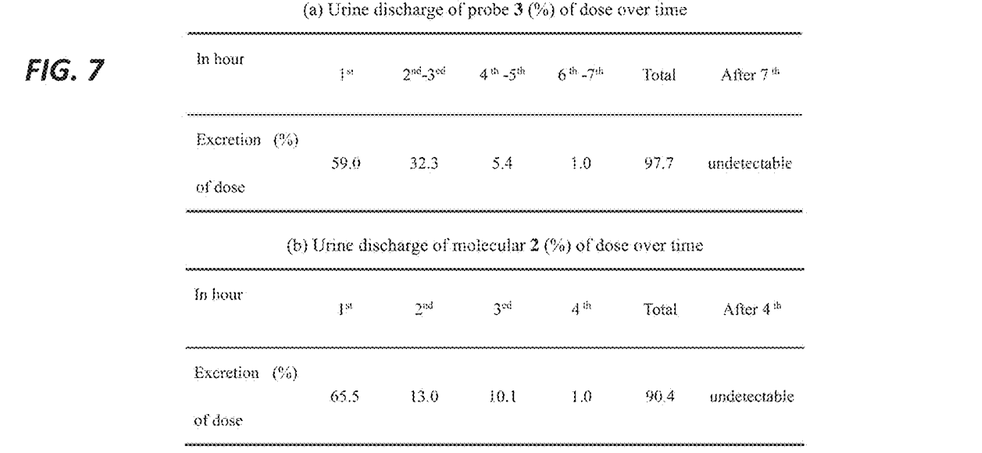

For reference, FIG. 4 shows a non-limiting example of the use of the CLI probe of the present invention for detection of a target cell of interest. HRP-labeled antibodies specific for a particular cell receptor on the target cell of interest are introduced to a subject. The CLI probe (e.g., compound 3) of the present invention is also introduced to the subject. The oxidation of the CLI probe via the HRP molecule produces detectable chemiluminescence, thereby detecting the target cell of interest (and optionally localizing the target cell of interest).

To test the probe in vivo, a PBS solution of the CLI probe (compound 3) was administered into nude mice through either intraperitoneal (IP) or intravenous (IV) injection (IP and IV injection had comparable uptakes). Images showed clear CLI of endogenous ROS in the mice. The IP-administered probe was found to diffuse across the peritoneal membrane, be absorbed into the veins, and be delivered to various sites of interest via blood circulation, e.g., kidney, liver, lungs, brain, stomach, heart, spleen, intestine. It appeared that compound 3 was more sensitive to various ROS as compared to luminol (see FIG. 5, FIG. 6). In three hours, about 90% of the probe was cleared by uresis, and in about seven hours the probe in its original form was completely flushed out (see FIG. 7). Without wishing to limit the present invention to any theory or mechanism, it is believed that the quantitative recovery of the intact probe suggests that the oxidation of the probe by endogenous $H_2O_2$ is kinetically sluggish in the time between its administration and clearance (e.g., because a live body is a natural producer of $H_2O_2$ due to the rapid decomposition of other ROS). A similar profile of clearance was obtained when the oxidized product (compound 2), the ground-state luminophore, was directly administered (see FIG. 7). These results suggest that both the probe and its oxidation product (compound 2) are not quickly metabolized during the imaging procedure. It does not appear that the probe or the resulting luminophore has significant acute toxicity.

Figure 8:
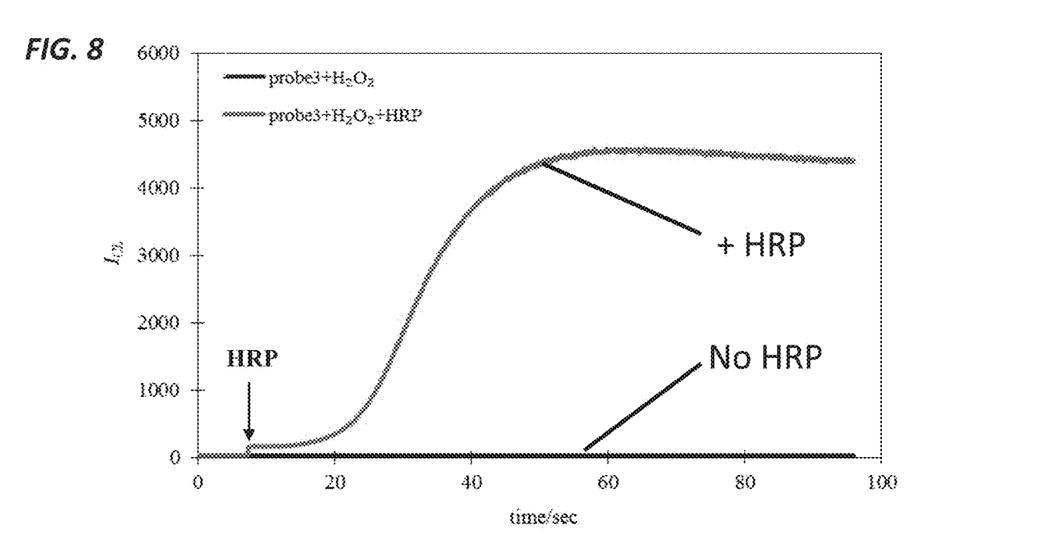

In the present invention, it was found that the otherwise sluggish kinetics of the oxidation of the probe by $H_2O_2$ could be enhanced by a trace amount of HRP (see FIG. 8).

Figure 9A:
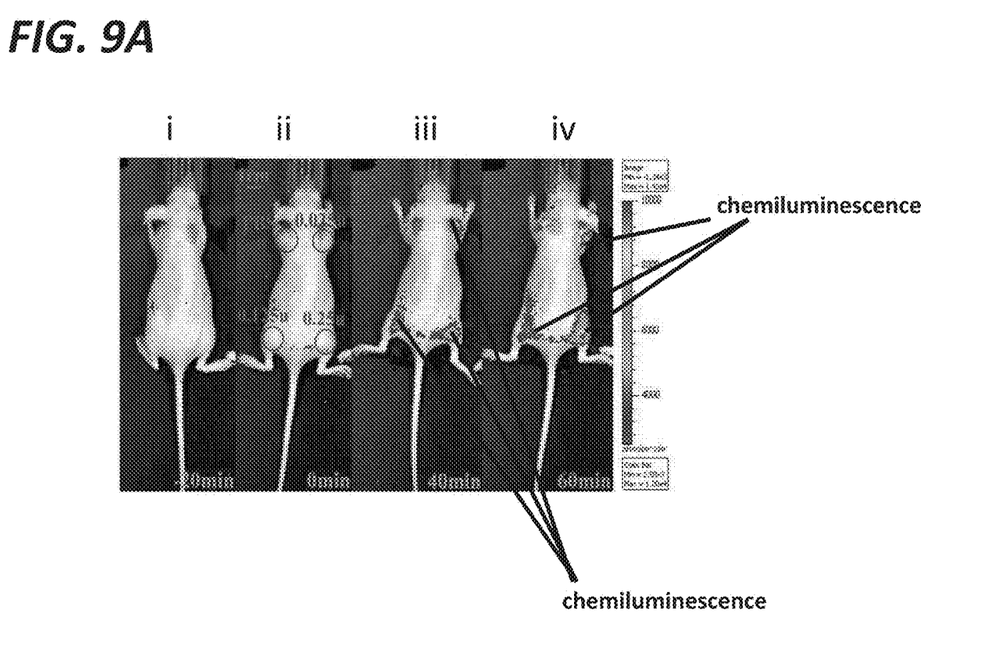
Figure 9B:
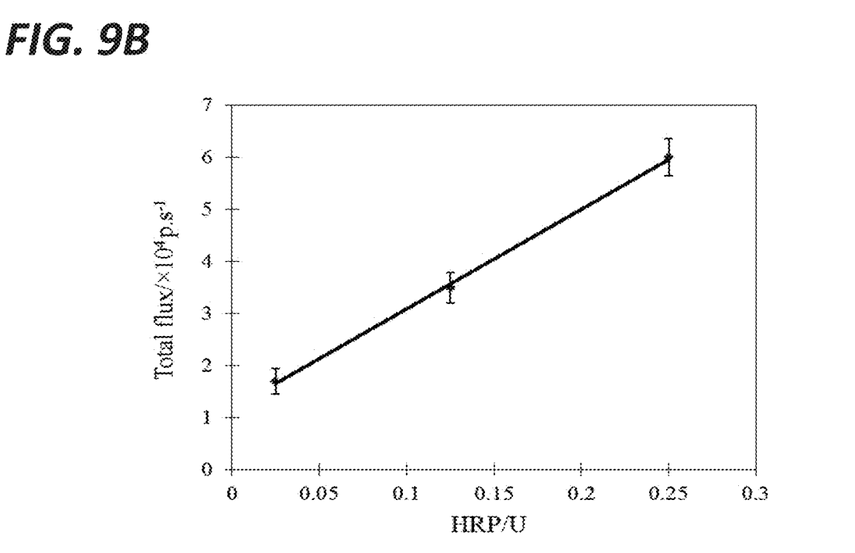

Imaging of HRP was acquired in nude mice pre-injected with compound 3 (720 μg per kg body weight) against a control mouse intraperitoneally injected with luminol. As compared to a PBS-only control (PBS was injected into the left foreleg), strong CL emissions were observed in the other legs in which HRP in PBS was subcutaneously introduced. (The total activity of HRP introduced into the right foreleg, the left hind leg, and the right hind leg were 12.5, 25.0, and 50.0 U, respectively; the moment when the administration of compound 3 was completed was set as −20 min with 0 min being the moment when the subcutaneous injection of HRP was finished.) In mice, it was found that CL could be detected with a dosage of compound 3 of about 2 µg/kg. To achieve significant CL intensity and to assure the accuracy of photon counting, the probe at a concentration of 720 µg/kg was used in subsequent studies in nude mice whose right foreleg, left hind leg, and right hind leg were injected with HRP of a total activity of 12.5 U, 25.0 U, and 50.0 U, respectively. Significant luminescence was produced and remained stable in a time window of 40 to 120 minutes following the introduction of HRP in each of the legs (data not shown). Production of CL appeared to be saturated when the activity of the enzyme was at about 25.0 U and above (without wishing to limit the present invention to any theory or mechanism, it is believed that this may have been because of the amount of endogenous $H_2O_2$ present in the mice).

In subsequent experiments, a dose of 7.2 mg/kg of compound 3 was used with which a total activity of HRP as low as 0.025 U could be detected. The CL produced intensified as the concentration of HRP increased, yielding a positive linear relationship.

Figure 10:
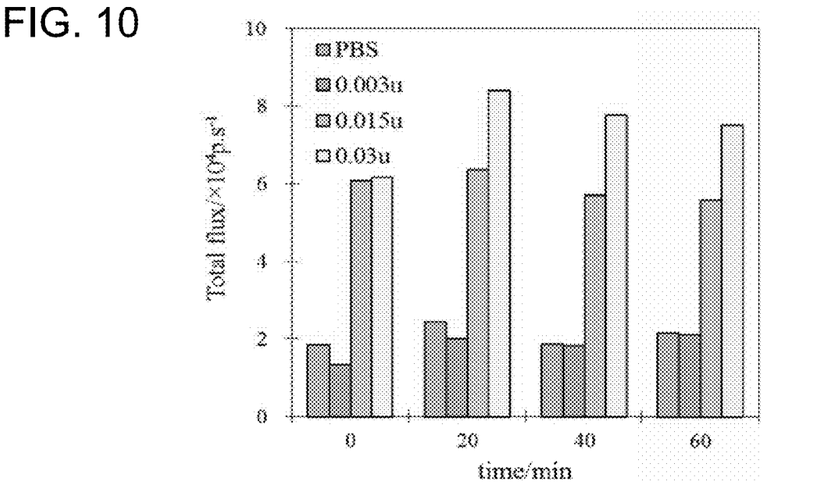
FIG. 10 shows photon counts measured 20, 40, and 60 minutes following the administration of the HRP-Ab conjugate.
Figure 11:
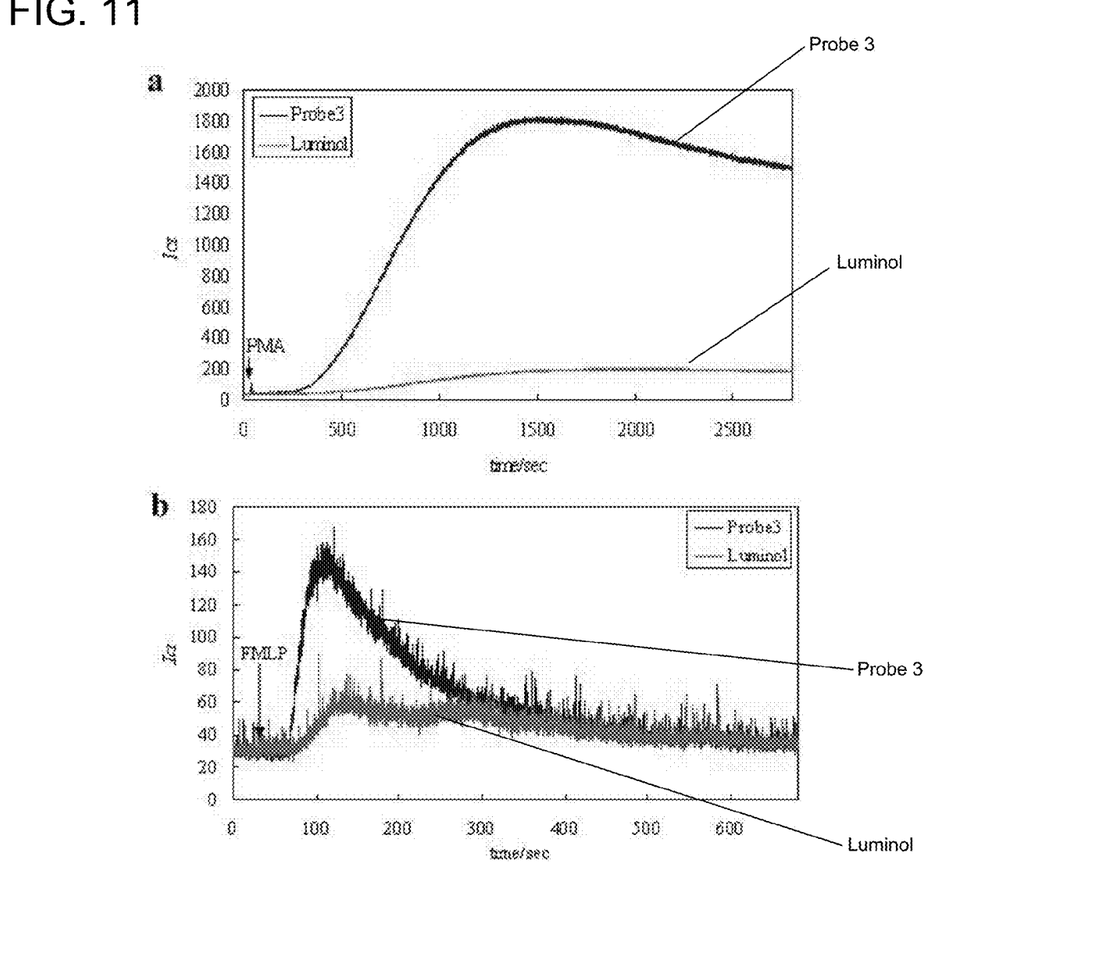

The use of the probe was validated using an enzyme-linked immunosorbent assay (ELISA) by imaging in nude mice the HRP-labeled goat anti-mouse IgG (HRP-Ab), a commercially available and commonly used HRP-antibody conjugate. To assess the sensitivity of the CLI, different amounts of the conjugate were administered to three of the legs of a nude mouse with the left foreleg injected with PBS only being the control. (Compound 3 was intraperitoneally injected at a dose of 7.2 mg per kg body weight; Against the HRP-Ab-free and PBS-only control in the left foreleg, the amounts of HRP-Ab administered into right foreleg, left hind leg, and right hind leg are 0.0030, 0.015, and 0.030 U, respectively.) FIG. 10 shows photon counts measured 20, 40, and 60 minutes following the administration of the HRP-Ab conjugate. The brightness of the emission is proportional to the amount of HRP-Ab present. It appeared that the amount of HRP-Ab present in the right foreleg was inadequate to produce any significant photon count or luminescence. However, in the two hind legs, whose total activity of HRP is at 0.015 and 0.030 U, respectively, the emission of light was vivid, and the reduction in luminescence intensity was only about 10% after 60 minutes following the probe administration.

Figure 12:
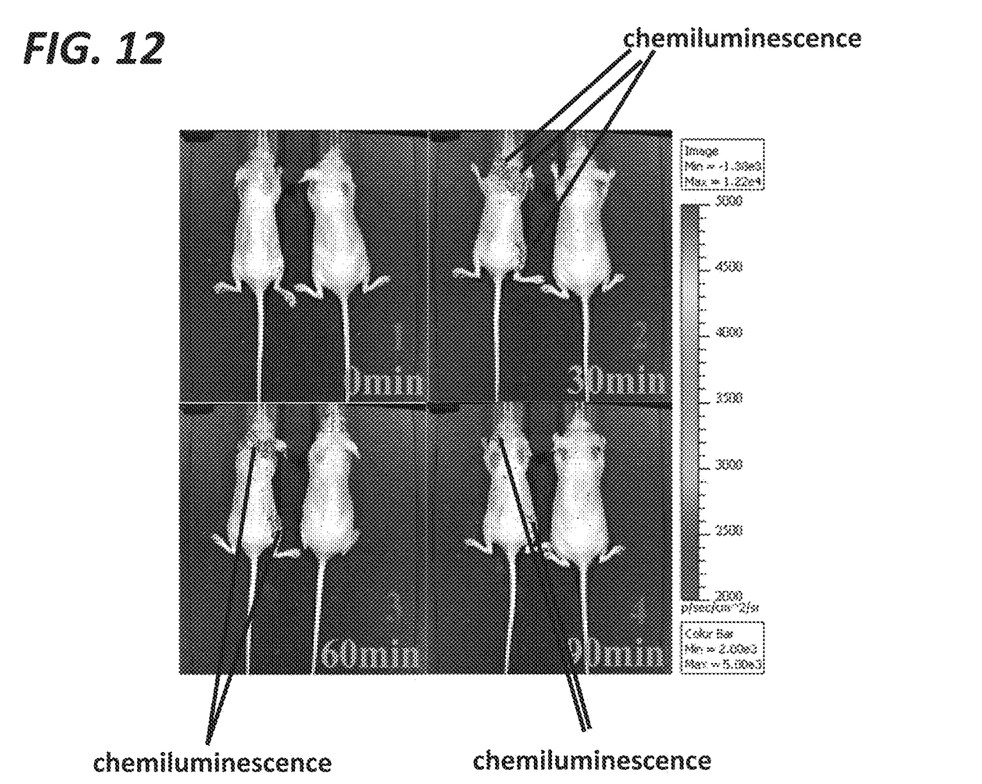
FIG. 12 shows CLI of acute dermatitis induced by topically daubing dimethylbenzene onto the head and the right hind leg of the test mice. The right mouse in each pair is the control with the administration of luminol. Images numbered 1-4 were taken before probe administration and 30, 60, and 90 min after the administration of compound 3 or luminol. The dosage of the administered compound 3 or luminol is 720 μg/kg.

The use of the CLI probe of the present invention (compound 3) in a clinical application (e.g., inflammatory response) has been explored. For example, the phagocyte respiratory burst or the release of ROS was monitored in vitro (see FIG. 11). FIG. 12 shows the in vivo results of CLI for acute dermatitis using compound 3 (luminol was the control). Images were taken 30, 60, and 90 minutes following the administration of either compound 3 or luminol. It appears that compound 3 was highly efficient in producing CLI of the acute dermatitis induced by dimethylbenzene, while luminol failed to produce any detectable signals.

Additional experiments were carried out using test mice suffering from gingival hemorrhage and mechanical injury. For example, nude mice were fed with cooked yolk for 1 week until gingival hemorrhage was visually identified. Various images were acquired (e.g., 0, 20 (supine position), and 30 min (prone position)) after the injection of 200 µL of $2.0 \times 10^{-4}$ M probe 3 or luminol (data not shown). The sites of inflammation were clearly identified by the luminescence at the sites using compound 3. Also, images of injuries (e.g., mechanical crush and syringe needle piecing, both on the end to tail) were acquired 0, 20, and 40 min, respectively, after the injection of 200 µL of probe 3 ($2.0 \times 10^{-4}$ M). Again, the sites of inflammation were clearly identified by the luminescence at the sites using compound 3.

Furthermore, inflammation caused by intramuscular injection of PBS was also clearly imaged using probe 3 and in comparison with results using PET/CT (data not shown). Nude mice were intramuscularly injected with PBS two days prior to said imaging experiments. For the verification of the induced inflammation, 18-Fluorodeoxyglucose-Positron emission tomography/Computed tomography (18FDG-PET/CT) scan, from feet to head, was performed 12 h after the CLI experiment. The test mouse was anesthetized with isoflurane inhalation followed by intraperitoneal injection of 3.7 MBq of $^{18}$FDG. An uptake time of 60 min was allowed before acquisition. As previously described, compound 3 clearly showed inflammation (images not shown).

These results support the use of compound 3 as a sensitive probe for noninvasive assessment of localized inflammatory responses.

Example 1

Example 1 describes methods and reagents for use in the present invention. The present invention is not limited to the methods, devices, systems, molecules, compositions, or other components disclosed herein.

Reagents.

Pyromellitic acid and m-dihydroxybenzene were obtained from Quzhou Rainful Chemical Co. Ltd. Luminol (≥97% HPLC grade), phorbol-12-myristate-13-acetate (PMA, for molecular biology), horseradish peroxidase (HRP, BR), and xanthine oxidase (BR) were purchased from Sigma-Aldrich. TNFα(h) ELISA kit was purchased from Wuhan Boster Bio-engineering Co. Ltd. Peroxidase-conjugated affinipure goat anti-mouse IgG(H+L) (ZB2305) was purchased from ZSGB-Bio Inc. Hydrogen peroxide (30% aqueous solution), xanthine, dimethylbenzene and hydrazine hydrate, all of analytical purity, were obtained from Sinopharm Chemical Reagent Co, Ltd. (SCRC). Isoflurane was obtained from Lunan Better Pharmaceutical Co., Ltd.

Preparation of Test Solutions.

Solids of compound 3 or luminol were dissolved in 0.01 M NaOH to a final concentration of $8.0 \times 10^{-3}$ M, and the resulting solutions were stored at 4° C. in the absence of light. The solutions were further diluted by using sterile phosphate-buffered saline (PBS, 0.01 M and pH 7.4) as desired in various studies. PMA was dissolved in DMSO to prepare 500 □g/ml solution. HRP was freshly prepared by dilution using sterile PBS.

Instrumentation. NMR spectra were obtained by using a 300 or 600 MHz spectrometer (Bruker BioSpin International AG, Zug, Switzerland). High-resolution Mass Spectrometric (HRMS) analyses were performed on an electrospray time-of-flight tandem mass spectrometer (maXis, Bruker Daltonics Inc. MA, USA). Chemiluminescence was measured using an MPI-A chemiluminescence instrument (Remex Analytical Instrument Co. Ltd., Xi'an, China). Fluorescence and chemiluminescence spectra were recorded using a 970 CRT fluorospectrophotometer (Shanghai Analytical Instrumental Ltd., China). The imaging system used was Xenogen IVIS 200 (Xenogen Corp. CA, USA). $^{18}$F-FDG PET/CT was performed using a Mediso Nanoscan PET/CT (Mediso Ltd. Budapest, Hungary).

Synthesis of Compound 2.

(Jiao, G., Castro, J. C., Thoresen, L. H. & Burgess, K. Microwave-assisted syntheses of regioisomerically pure bromorhodamine derivatives. Org. Lett. 5, 3675-3677 (2003)). Pyromellitic acid was dissolved in acetic oxide, and the resulting solution was brought to and maintained under reflux for 6 h. The reaction mixture was then cooled to room temperature and filtered. The yellow solid collected, raw pyromellitic dianhydride, was washed with diethyl ether and dried in vacuo. A sample of this solid (5.45 g, 0.025 mol) was then added to a melt of resorcinol (5.5 g, 0.050 mol) at 150° C. with vigorous stirring. Fused $ZnCl_2$ (6.80 g, 0.050 mol) was then added slowly, and the temperature of the resulting mixture was slowly raised to 180° C. over 20 min until the reaction mixture solidified. The brick red solid was pulverized and extracted in 100 mL of 0.5 M HCl for 1 h. The red solid was collected, washed with water and dried in vacuo. Crude product was subjected to column chromatography on silica gel with 1:2 (volume ratio) concentrated ammonia/isopropanol as the eluting solution. Isolated yield: 31.4%. $^1$H NMR (DMSO-$d_6$, 300 MHz) δ 10.17 (s, 2H), 8.29 (d, J=15.0 Hz, 1H), 7.52 (s, 1H), 6.67 (dd, J=7.9, 5.5 Hz, 4H), 6.56 (dd, J=8.7, 2.3 Hz, 2H). $^{13}$C NMR (DMSO-$d_6$, 600 MHz) δ 167.35, 159.73, 154.60, 151.75, 140.51, 133.94, 129.32, 127.49, 125.55, 123.94, 112.70, 108.49, 102.28, 83.47. HRMS [M−H]$^−$ calcd for [$C_{22}H_{11}O_9$]$^−$ 419.0401; found 419.0392.

Synthesis of Probe 3.

A solution of compound 2 (2.24 g, 0.0050 mol) and 10% hydrazine hydrate (2.4 mL, 0.0050 mol) in 14 mL of triethylene glycol was vacuumed at 100° C. for 30 min. The solution was then heated to 180° C. and maintained at this temperature for 1.5 h. The product mixture was subjected to silica column chromatography using a mixture of ($CH_3COOC_2H_5$:$CH_3OH$:HAc=8:0.1:0.0125) as the eluting solvent. Isolated yield: 72.7%. $^1$H NMR (300 MHz, DMSO-$d_6$) δ 11.98 (s, 1H), 10.20 (s, 2H), 8.57 (s, 1H), 7.76 (s, 1H), 6.71 (d, J=2.3 Hz, 2H), 6.66 (d, J=8.7 Hz, 2H), 6.53 (dd, J=8.7, 2.3 Hz, 2H). $^{13}$C NMR (MeOD, 600 MHz) δ 182.72, 173.44, 161.32, 160.25, 159.20, 144.91, 137.92, 132.29, 131.20, 131.04, 128.78, 128.22, 124.31, 113.14, 104.54, 73.29, 70.88. HRMS (ESI) [M+H]$^+$ calcd for [$C_{22}H_{13}N_2O_7$]$^+$ 417.0724; found m/z=417.0729.

Imaging in Mouse Models.

Nude mice used in this work, each weighing 20-26 g, were obtained from the Laboratory Animal Center of the Fourth Military Medical University, China. Research and animal sacrifice protocols are in accordance with the principles and guidelines adopted by the Fourth Military Medical University. The mice were kept for an acclimatization period of 7 days under laboratory conditions (temperature maintained at 22±2° C., 12-hr cycles of alternating illumination and darkness, and free access to food and water) prior to any imaging experiments. Nude mice were anesthetized by isoflurane inhalation, following which 200 μL of a solution of compound 3 or luminol in PBS of pH 7.4 was injected intraperitoneally. For the imaging of HPR or HRP-Ab, the probe solution (2.0×10$^{-3}$ M) was first injected, followed by the subcutaneous injection 20 minutes after of PBS and HRP (variable amount in 0.01 M PBS) solutions into the legs of nude mice. The control experiments with the use of luminol were conducted under otherwise identical conditions. IVIS 200 bioluminescence imaging system (Caliper Life Sciences) (f/stop, 1; no optical filter) was used for all imaging experiments. Exposure time was set at 5 minutes with moderate sensitivity, and the binning and field of view (FOV) are 8 and 13.3 cm, respectively. Photon counts were integrated by using the system-provided software.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. A chemiluminescence imaging (CLI) probe according to Formula I,

Formula 1 wherein any of $R_1$-$R_8$ are H, —OH, —COH, —COOH, or a halide.

2. The CLI probe of claim 1, wherein the CLI probe comprises Compound 3, as shown below, Compound 3

3. The CLI probe of claim 1, wherein the CLI probe is soluble.

4. A kit comprising
 a. a chemiluminescence imaging (CLI) probe according to Formula 1, wherein any of $R_1$-$R_8$ are H, —OH, —COH, —COOH, or a halide; and
 b. a first binding molecule labeled with horseradish peroxidase (HRP) or myeloperoxidase (MPO).

5. The kit of claim 4, wherein the first binding molecule comprises an antibody or a fragment thereof.

6. The kit of claim 4, wherein the first binding molecule comprises a ligand.

7. A method of detecting inflammation in a subject, said method comprising:
 a. introducing to the subject a chemiluminescence imaging (CLI) probe according to Formula 1, wherein any of $R_1$-$R_8$ are —H, —OH, —COH, —COOH, or a halide; and
 b. introducing to the subject a first binding molecule labeled with a ROS, said first binding molecule is specific for an inflammatory molecule, wherein the CLI probe is adapted to be oxidized by the ROS thereby emitting chemiluminescence, wherein chemiluminescence is indicative of the presence of the inflammatory molecule.

8. The method of claim 7, wherein the ROS comprises HRP.

9. The method of claim 7, wherein the CLI probe is administered before the first binding molecule is administered.

10. The method of claim 7, wherein the first binding molecule is administered before the CLI probe is administered.

* * * * *